United States Patent [19]
Scott et al.

[11] Patent Number: 4,873,862
[45] Date of Patent: Oct. 17, 1989

[54] IONIZATION DETECTORS FOR GAS CHROMATOGRAPHY

[75] Inventors: Raymond P. W. Scott, Avon; Elena Katz, Westport, both of Conn.

[73] Assignee: The Perkin-Elmer Corporation, Norwalk, Conn.

[21] Appl. No.: 4,810

[22] Filed: Jan. 9, 1987

Related U.S. Application Data

[63] Continuation-in-part of Ser. No. 852,489, Apr. 16, 1986, abandoned, which is a continuation-in-part of Ser. No. 808,965, Dec. 16, 1985, abandoned.

[51] Int. Cl.⁴ ............................................. G01N 31/08
[52] U.S. Cl. ...................................... 73/23.1; 250/382
[58] Field of Search ................. 73/23.1; 250/382, 383, 250/389; 324/464, 665, 470

[56] References Cited

U.S. PATENT DOCUMENTS 3,243,991 4/1966 Konig et al. .......................... 73/23.1
4,063,156 12/1977 Patterson ............................ 250/382
4,500,786 2/1985 Britten et al. ....................... 250/389
4,527,064 7/1985 Anderson ............................ 250/389

OTHER PUBLICATIONS

C. H. Deal et al. "A Radiological Detector For Gas Chromatography", Analytical Chemistry, vol. 28, No. 12, pp. 1958–1964, Dec. 1956.

Primary Examiner—Stewart J. Levy
Assistant Examiner—Hezron E. Williams
Attorney, Agent, or Firm—E. T. Grimes; F. L. Masselle; R. G. Cummings

[57] ABSTRACT

It has been discovered that a glass envelope at elevated temperature containing a noble gas will result in electrons being evolved. The phenomenon has been employed to construct both argon and helium detectors for gas chromatography.

14 Claims, 8 Drawing Sheets

① n-PENTANE
② n-OCTANE
③ n-DECANE
④ n-DODECANE
⑤ n-TRIDECANE
⑥ n-TETRADECANE
⑦ DIBUTYLPHENOL
⑧ n-HEXADECANE

FIG. 12

IONIZATION DETECTORS FOR GAS CHROMATOGRAPHY

PRIORITY

This is a continuation-in-part of co-pending application Ser. No. 852,489 filed on Apr. 16, 1986 which is a continuation-in-part of Ser. No. 808,965 filed Dec. 16, 1985, now abandoned.

TECHNICAL FIELD

This invention pertains to gas chromatography detectors and, more particularly, to such detectors of the ionization type.

BACKGROUND ART

Ionization detectors for gas chromatography are well known in the art. A comprehensive survey of such detectors as of 1961 may be found in an article entitled "Ionization Methods for the Analysis of Gases and Vapors" by J. E. Lovelock, Analytical Chemistry, Volume 33, No. 2, February 1961, pages 162–178. The detectors reviewed in that article include, inter alia, the cross-section ionization detector, the argon detector, and the electron capture detector. These detectors are characterized by the fact that each includes a source of ionizing radiation, i.e., a radioactive material.

The use of radioactive substances in chromatographic detectors necessarily introduces certain health risks into the laboratory and complicates such tasks as cleaning detectors after use. Because of these health risks, they are also subject to certain governmental controls which complicate their application and use.

Ionization detectors have been developed which avoid the need for radioactive elements. However, in many cases, these are not suitable for use as argon and electron capture detectors for various reasons, among which is the fact that they may require other gasses in addition to the carrier or sample. Examples are the photo-ionization detector referenced in the above-mentioned Lovelock article and the flame ionization detector (FID).

An electron capture detector has been developed which utilizes a filament as a thermionic emission electron source. Such a detector is described in U.S. Pat. No. 4,304,997 of Sullivan et al. However, there are certain problems inherent in such a thermionic detector. One such problem is that the emitting filament is at very high temperature, is of limited area, and may be "poisoned" by components of many samples—i.e., components may be adsorbed on the surface and thereby reduce its thermal emissivity.

In a more recent development, electrons for use in argon and cross-section detectors have been produced by the action of ultraviolet radiation on a suitable metallic surface. Such a detector has functioned satisfactorily but required an ultraviolet source, windows transparent to ultraviolet radiation, and satisfactory electron emitting surfaces.

For the foregoing reasons, it is a primary object of this invention to provide an ionization detector which avoids the need for ionizing or optical radiation, additional gases, heated filaments, or dedicated electron sources. Other objects, features, and advantages will become apparent from the following description and appended claims.

DISCLOSURE OF INVENTION

An exemplary embodiment of the present invention is a detector for use in gas chromatography, of the type having a detection chamber across which an electrical potential is impressed. A volume of glass defines the chamber in whole or in part or is adjacent thereto, and a noble gas is caused to flow through the chamber in contact with the glass. The temperatures of the gas and the glass volume are raised to a value between at least 120° C. and, to a maximum established by practical considerations, e.g., softening of the glass, etc.

BRIEF DESCRIPTION OF DRAWINGS

FIGS. 2($a$), 2($b$) are graphs of the ionic current versus electrode voltage of the detector of FIG. 1;

FIGS. 7($a$) and 7($b$) are graphs of the response of the detector of FIG. 1 relative to the response of a flame ionization detector;

BEST MODE FOR CARRYING OUT THE INVENTION

In the original argon detector proposed by Lovelock, the base electron current was achieved by the use of a radioactive source and the electrons were accelerated across a high potential gradient between two electrodes, producing a cloud of metastable argon atoms in the process. When an organic vapor existed in the detector, collisons between the metastable argon atoms and the molecules of the vapor, produced electron-ion pairs and the current between the electrodes increased.

It has been discovered that at elevated temperatures, disposing a volume of glass in contact with a noble gas, results in the evolution of electrons in some manner. The temperature required is substantially less than that of a heated metal filament. The discovery has been employed to construct an ionization detector for gas chromatography.

Thermal evolution of electrons in a glass envelope at high temperatures was noted during experiments when currents were observed to pass through both argon and helium detector systems constructed of glass and operated at elevated temperatures. The current could not be accounted for by either photoelectric emission or thermionic emission from a metal surface. The phenomenon was verified by various experiments and was utilized to construct a detector. The principle on which the ionization detector functions is not clear at this time. It appears that at elevated temperatures emission of electrons from the glass surface in contact with the noble gas takes place and the electrons are accelerated under the potential gradient between electrodes. Due to the perfectly elastic nature of the collisions between electrons and noble gas atoms, the electrons pass through the noble gas and when reaching the energy appropriate to that of the metastable atom (11.6 electron volts for argon) uncharged metastable noble gas atoms are formed. When an organic vapor is present in the system, collision between a metastable noble gas atom and an organic molecule results in the ionization of the organic molecule accompanied by the return to ground state of the noble gas atom. As a consequence, an increase in ion current occurs between the electrodes, thus providing a signal indicating the presence of organic molecules.

Figure 1:
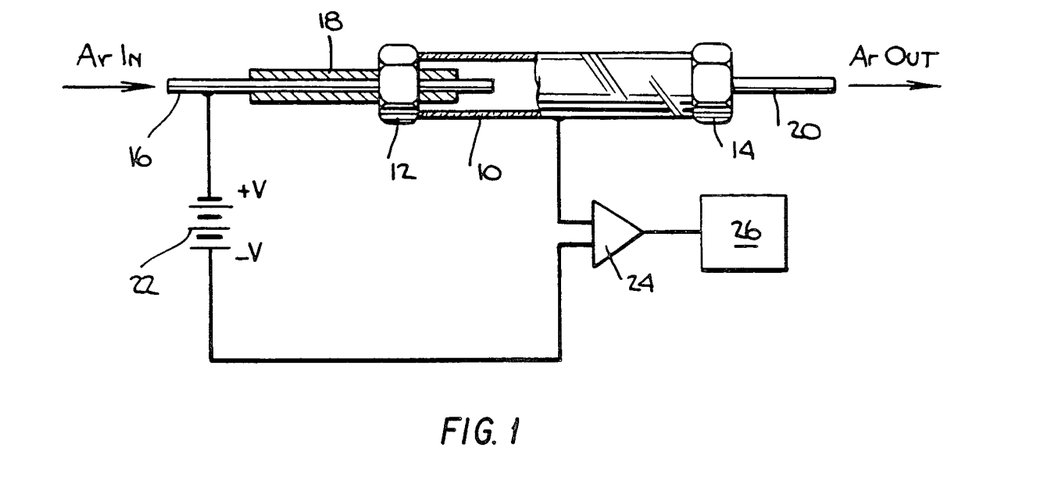
FIG. 1 is an illustration in partial cross-section of a noble gas detector in accordance with the present invention.

FIG. 1 illustrates an argon detector in accordance with the present invention. The detector comprises a cylindrical borosilicate glass tube 10. The ends of the tube 10 are terminated by stainless steel nuts 12, 14. The inlet end nut 12 carries a stainless steel inlet tube 16 having a polytetrafluoroethylene (PTFE) sleeve 18 for electrically insulating it from the nut 12. Inlet tube 16 is connected to receive the effluent from a chromatographic column (not shown). The exit end nut 14 carries a PTFE exit tube 20. The inlet tube 16 is connected to the positive terminal of a power supply 22 that can be varied between 0 and 2,000 volts. The negative side of the power supply is connected to the glass tube 10 through an amplifier 24 having a sensitivity range from $10^{-12}$ to $10^{-5}$ amps full scale deflection. The output of amplifier 24 is connected to a recorder 26. In one such detector, the stainless steel inlet tube 16 had an inside diameter of 0.038 cm and an outside diameter of 0.16 cm. The inlet tube projected into the glass tube 10 a distance of approximately 2 cm and had 1 mm of metal exposed beyond the end of the sleeve 18. The entire detector was enclosed within an oven having a temperature controllable from 40° C. to 400° C.

Figure 2:
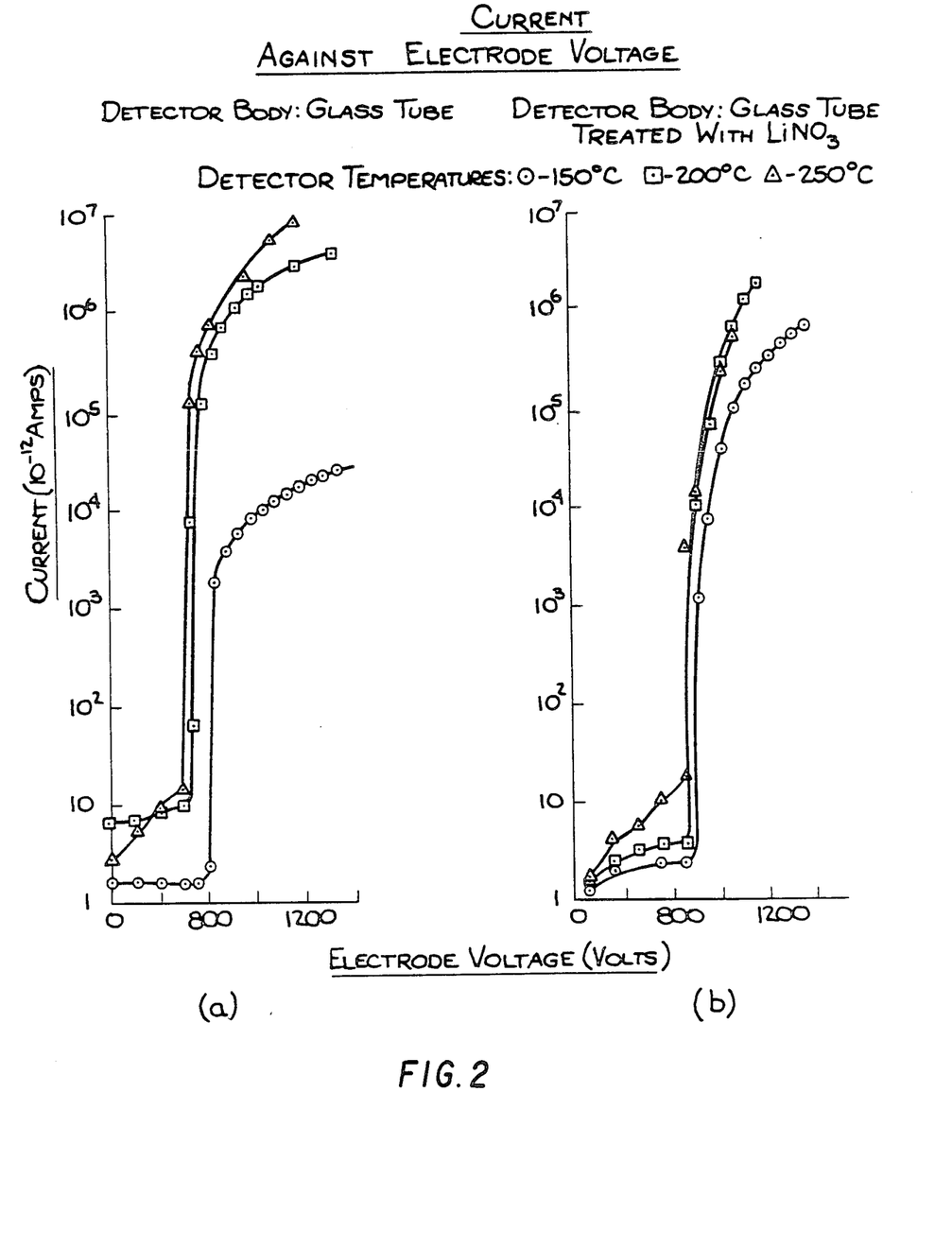

The detector of FIG. 1 was heated to various temperatures while passing therethrough air, nitrogen, or argon. No electric current could be detected when the detector was filled with air or nitrogen. The base current was measured in an atmosphere of argon over a range of different voltages at temperatures of 150° C., 200° C., and 250° C. The results are illustrated in the curves of FIG. 2(a). These experiments were repeated utilizing soda glass and quartz for the tube 10. Essentially similar results were obtained for the soda glass but no measurable current resulted when utilizing quartz, even in an argon environment. The use of helium in place of argon resulted in a current of approximately the same magnitude from both soda glass and borosilicate glass.

Figure 3:
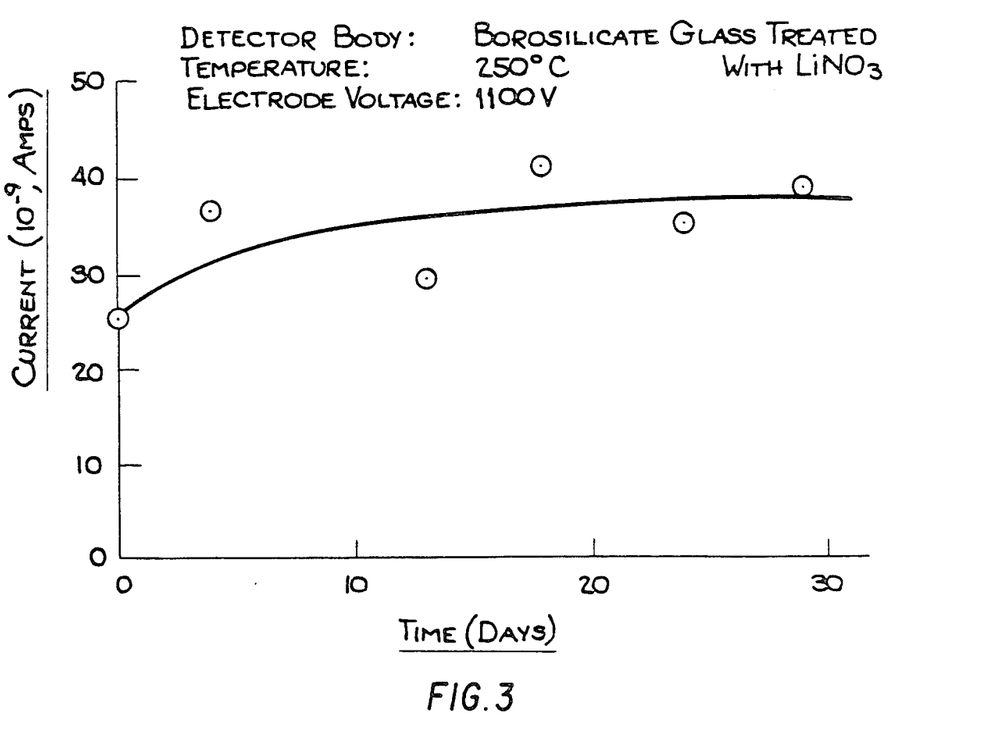
FIG. 3 is a graph of the change in standing current over time for the detector of FIG. 1.
Figure 4:
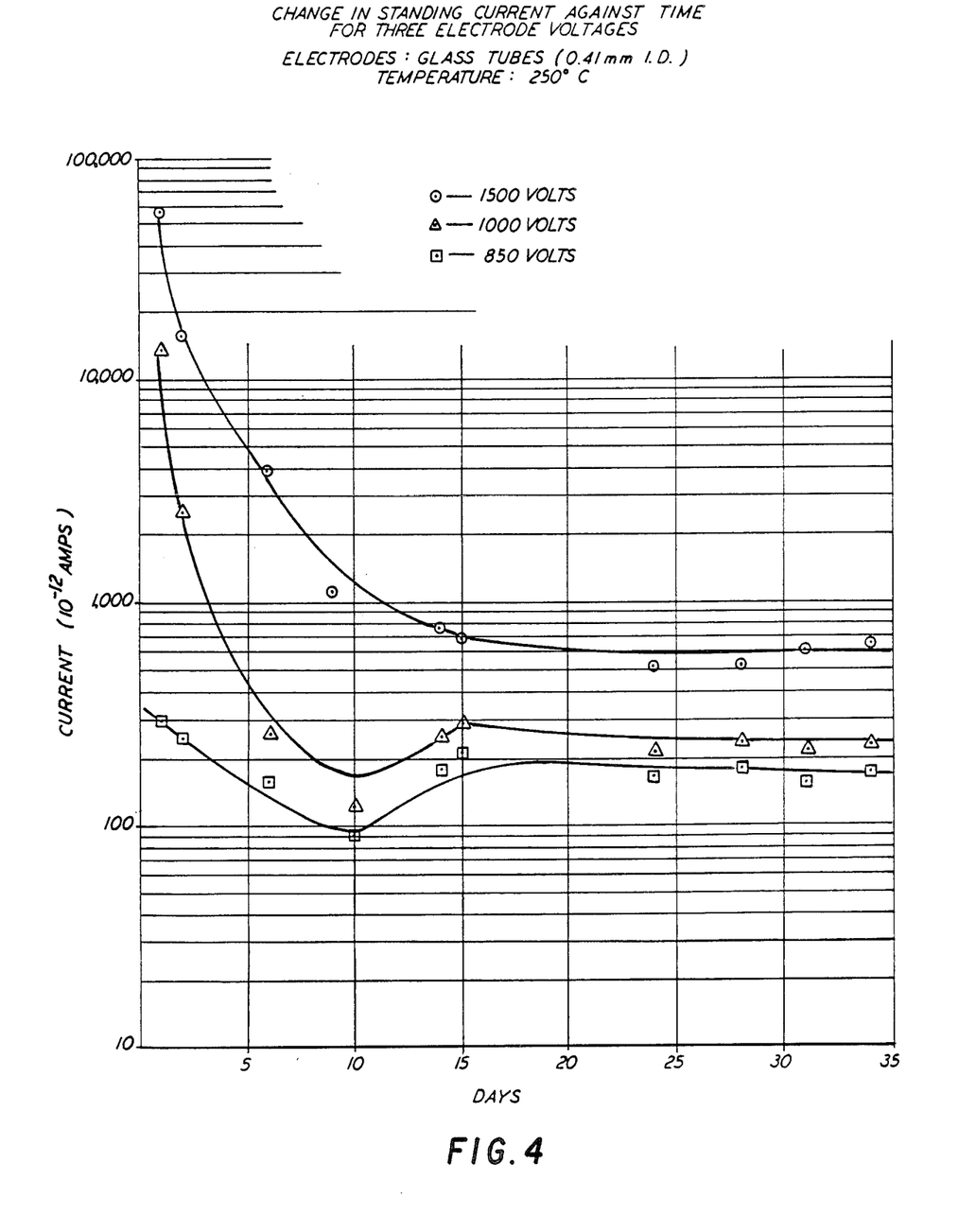
FIG. 4 is a graph of the change in standing current over time.

It was observed that the base current obtained varied considerably from day to day, as much as 100 percent from one day to the next. Upon the assumption that this might be a surface phenomenon, an attempt was made to stabilize the glass surface by treating it with an alkali metal salt such as lithium nitrate. The glass tube 10 was filled with fused lithium nitrate at 275° C. and allowed to stand for 15 hours. The lithium nitrate was then removed and the glass washed free of salt by sonication in methanol. Thereafter, measurements of current versus electrode voltage resulted in the curves shown in FIG. 2(b). The variation in base current with lithium treated borosilicate glass over a thirty day period is shown in FIG. 3. It is to be noted that the base current can be stabilized without the alkali metal salt treatment provided that an appropriate aging period is allowed. This is demonstrated in FIG. 3. Aging time varies inversely with aging temperature.

Figure 5:
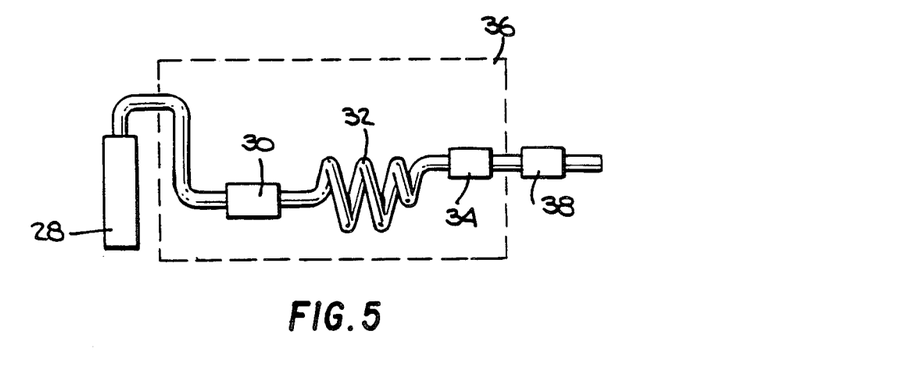
FIG. 5 is a schematic representation of the apparatus used to test the detector of FIG. 1.

The usefulness of this invention as a gas chromatography detector was tested by the apparatus of FIG. 5. It comprised an argon gas supply 28 connected through a septum injector 30 to the inlet end of a packed chromatographed column 32. The outlet end of the column 32 was connected to a detector 34 constructed as illustrated in FIG. 1 and described above. The column 32 and detector 34 were enclosed within a gas chromatograph oven 36. The exit gas from argon detector 34 was connected in series with a flame ionization detector (FID) 38 so that any solute vapor eluted through the system would be monitored by both detectors.

Figure 6:
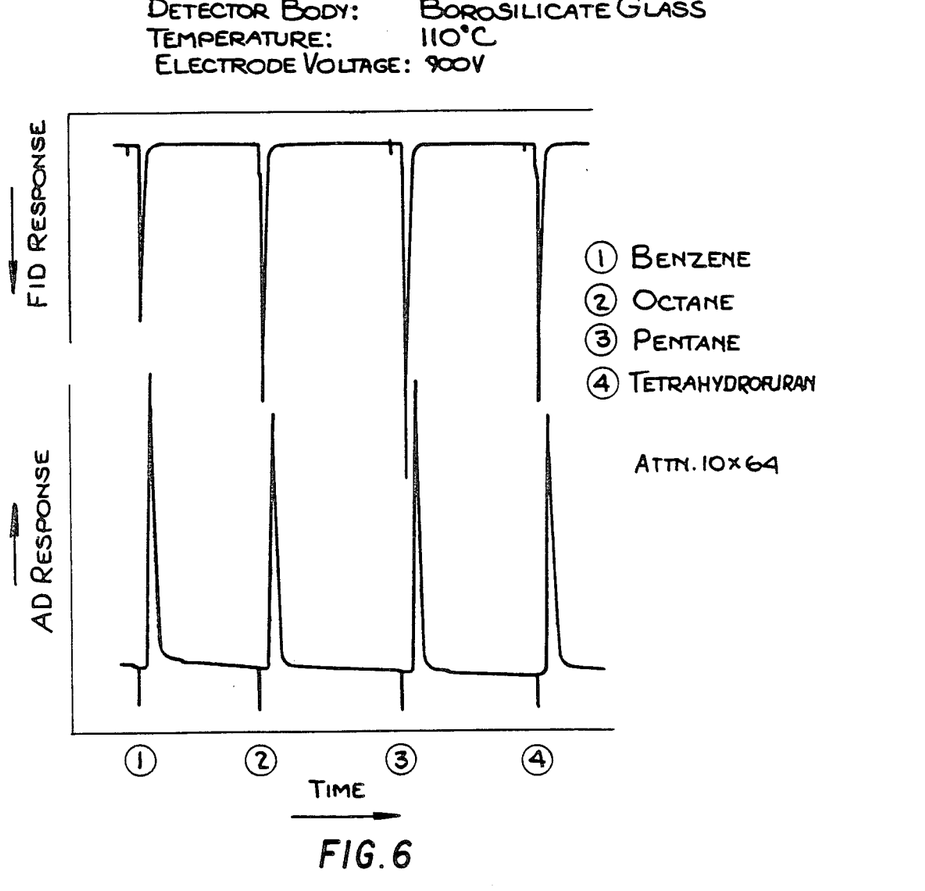
FIG. 6 illustrates the results of the tests conducted on the apparatus of FIG. 5.
Figure 7A:
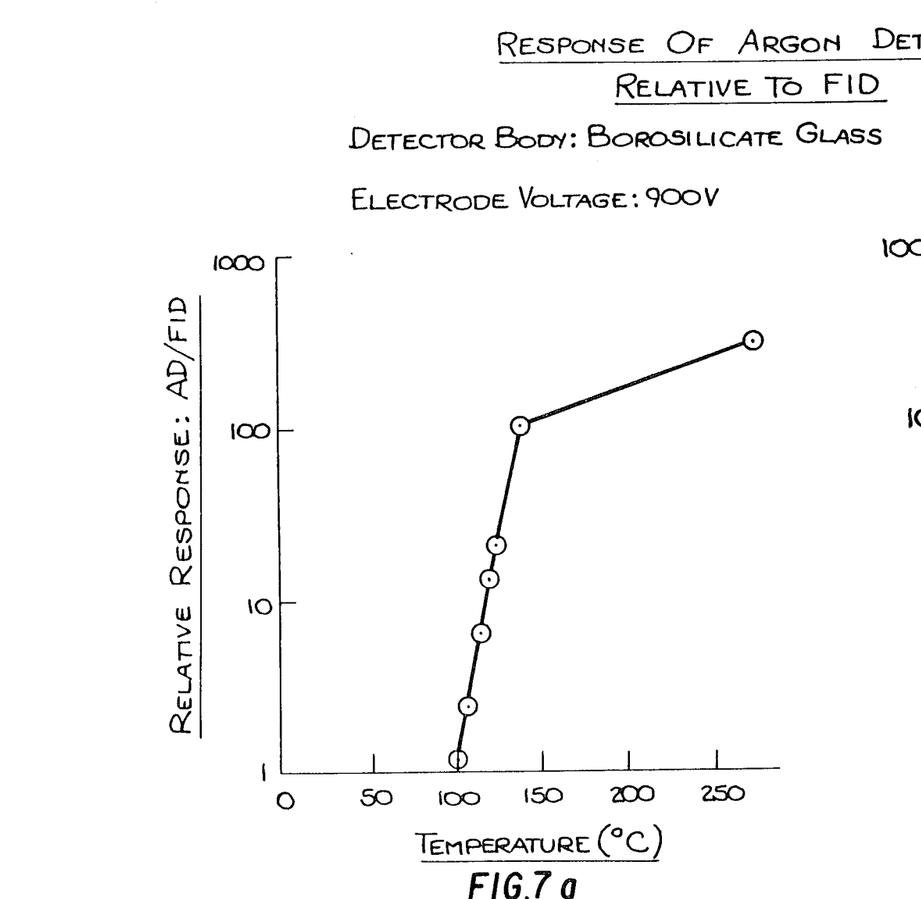

An example of the dual monitoring of four different hydrocarbons is shown in FIG. 6. Employing benzene as the solute, the response of the argon detector 34 was measured at an electrode potential difference of 900 volts and at temperatures ranging from 100° C. to 270° C. Shown in FIG. 7(a) are the same results, expressed as the ratio of the height of the peak obtained from the argon detector 34 in millivolts to that obtained from the FID 38 also measured in millivolts. The ratio of the noise of the argon detector 34 to that of the FID 38 was also measured and was found to be approximately two orders of magnitude.

Figure 7B:
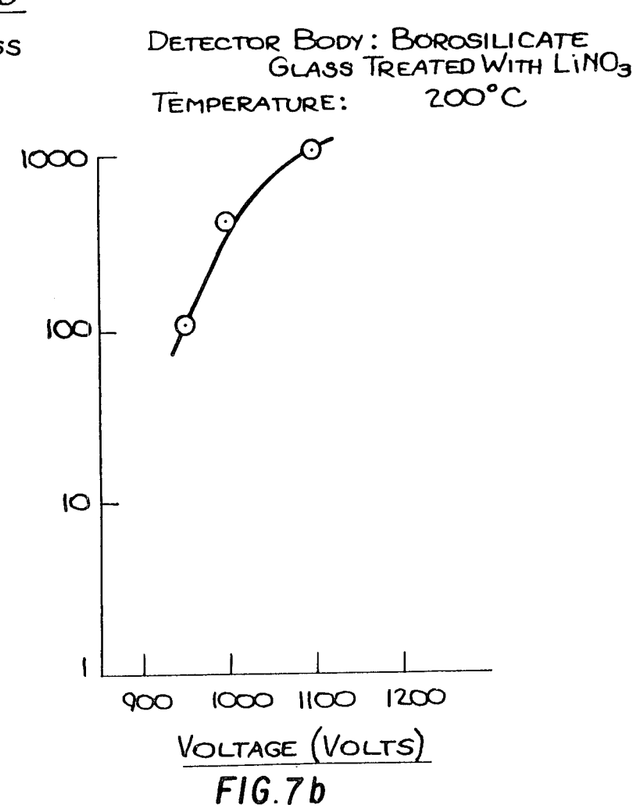

The relative response to the argon detector 34 to that of the FID 38 was also measured for the lithium nitrate treated glass. The detector 34 was held at a temperature of 200° C. and the electrode voltage varied between 950 volts and 1100 volts. The results, expressed as the ratio of the peak height obtained from the argon detector 34 to that from the FID 38, plotted against electrode voltage are shown in FIG. 7(b). The ratio of the noise from the argon detector 34 to that of the FID 38 remained at about two orders of magnitude.

The linearity of the response of the argon detector 34 relative to that of the FID 38 was determined by measuring the peak heights obtained from both detectors for a range of different charges of benzene. An untreated borosilicate tube was employed in the first instance at an electrode voltage of 900 volts. The measurements were carried out at detector temperatures of 100° C., 150° C. and 180° C. The results obtained are shown in FIG. 7 as curves relating the logarithm of the peak height obtained from the argon detector 34 to the logarithm of that obtained from the FID 38 for each of the three temperatures.

Figure 9:
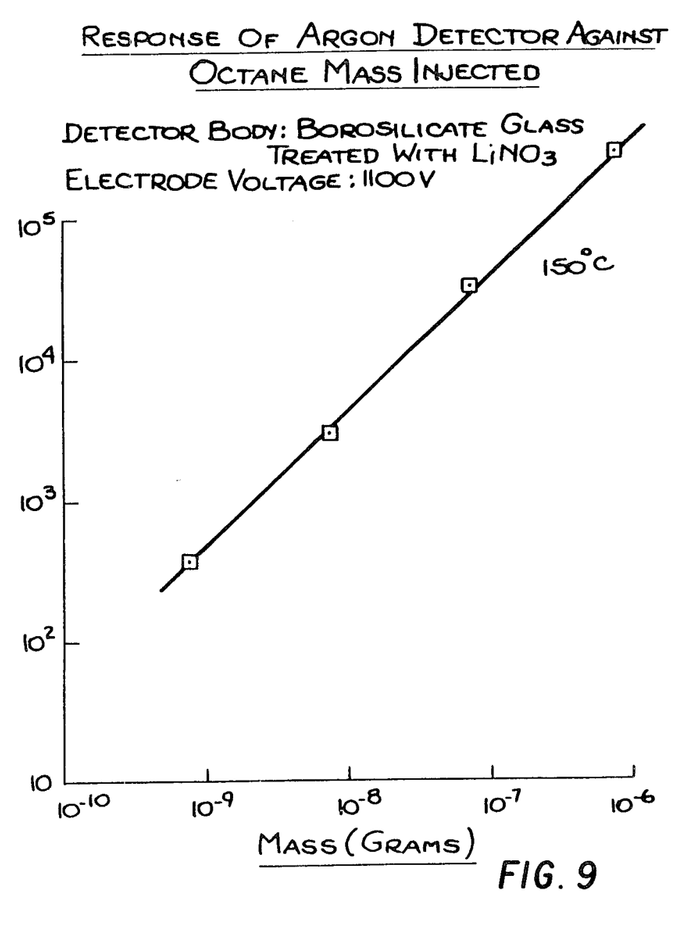
FIG. 9 is a graph of the response of the detector of the invention to injection of a sample quantity of octane.
Figure 12:
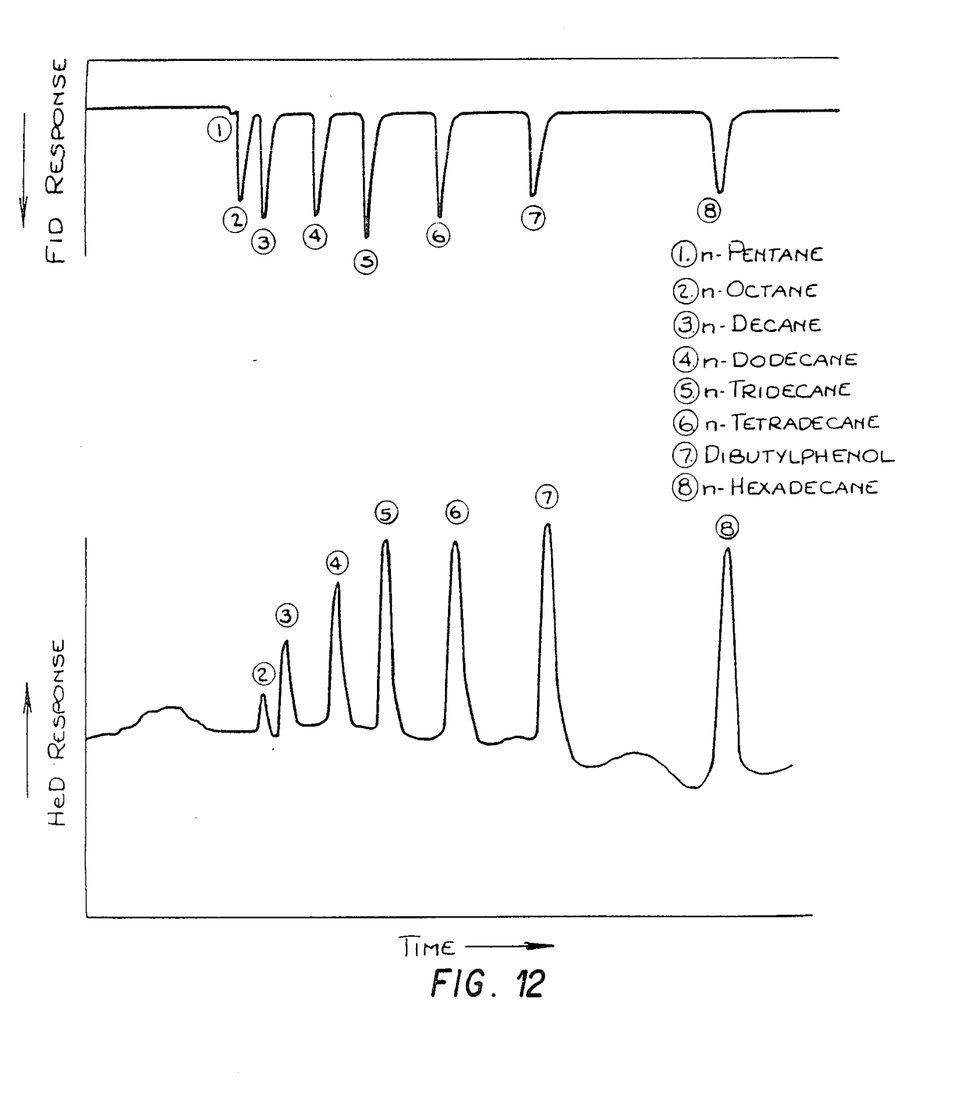
FIG. 12 is an illustration similar to FIG. 6 showing the results of a test on the apparatus of FIG. 10 using helium as the carrier gas.

The linearity of the response of the argon detector 4 with lithium nitrate treated glass was also determined in absolute units. The solute was n-decane and different masses were injected into the packed column 32 and the peak heights obtained from the argon detector 34 measured. The electrode voltage was 1100 volts and the detector temperature was 150° C. The results obtained are shown in FIG. 9 as curves relating the logarithms of the peak heights to the logarithms of the n-decane concentrations. The performance of the argon detector 34 when employed to monitor the separation of a high boiling hydrocarbon mixture in the packed column 32 at 200° C. is shown in FIG. 12.

The curves of FIGS. 2(a) and 2(b) indicate that, to obtain adequate base current for the production of metastable argon atoms, an electrode potential in excess of 900 volts was necessary. However, different geometries may permit such a detector to function at considerably lower electrode voltages. It would also appear that the operating temperature should be at least 150° C. for best results, although this limit may also depend on electrode configuration and electrode voltage. It will be noted that the current was relatively large, i.e., on the order of one microamp.

The borosilicate glass tube treated in the described example with lithium nitrate behaved in a very similar manner to the untreated tube, as seen by comparing the results shown in FIG. 2(a) with those shown in FIG. 2(b). From the results in FIG. 3, the lithium nitrate treated tube appeared to have stable properties over 30 days whereas the untreated tube gave widely varying base currents from day-to-day.

The results shown in FIG. 7(a) indicate the very significant increase in response of the argon detector 34 of this invention over that of a conventional FID at elevated temperatures. Those results are from a detector made from a borosilicate glass tube not treated with lithium nitrate. It should also be noted, however, that the noise level was two orders of magnitude greater than that of the FID, giving a signal-to-noise ratio approximately the same as that of the FID.

The results shown in FIG. 7(b) indicate that the lithium nitrate treated glass, operated at 200° C. and at higher electrode voltages, can provide a response three orders of magnitude greater than the FID. Furthermore, as the noise of the argon detector 34 remained only two orders of magnitude greater than that of the FID, the argon detector was exhibiting a sensitivity of at least one order of magnitude greater than the FID. It should be pointed out that this estimate of sensitivity is very conservative as the detector was not electrically screened or grounded in any way, and no attempt was made to minimize noise.

Figure 8:
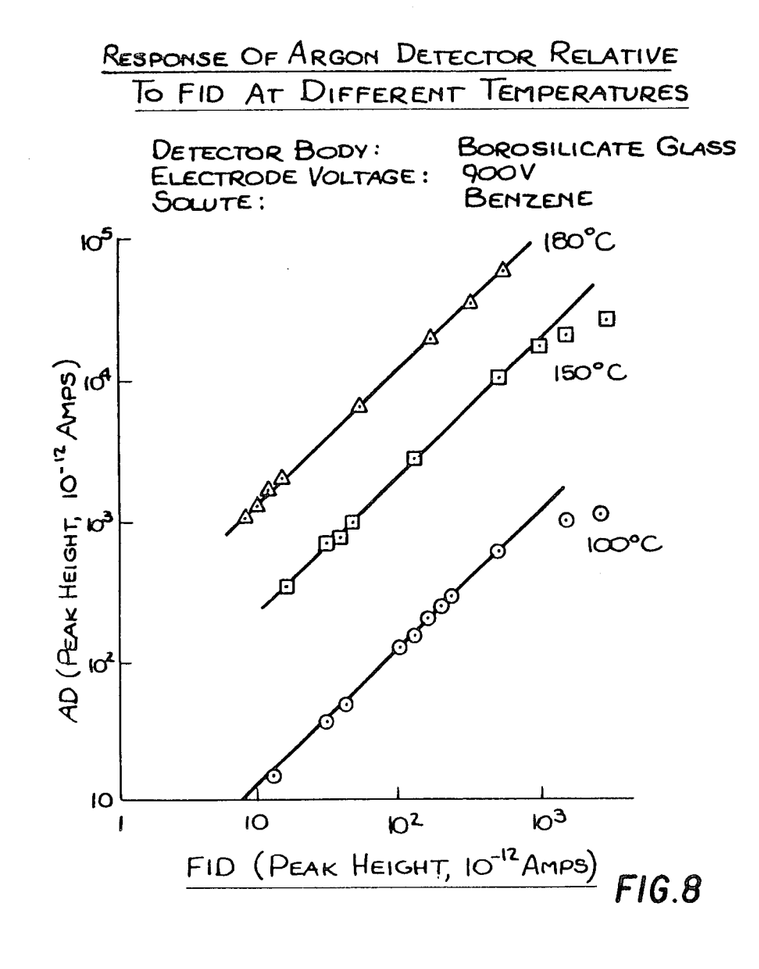
FIG. 8 is a graph of the response of the detector of this invention relative to that of a flame ionization detector at different temperatures.

The curves shown in FIG. 8 have slopes of 0.999, 0.986, and 0.994 at temperatures of 100° C., 150° C. and 180° C., respectively. Consequently, assuming the linearity of the FID, the response of the argon detector, employing untreated borosilicate glass was linear over at least two orders of magnitude of solute concentration. The curves shown in FIG. 9 are more significant, as they relate argon detector response to the actual concentration of solute injected. The curve in FIG. 9 is for the argon detector 34 with lithium nitrate treated borosilicate glass; the slope of the curve is 0.967, indicating a true linear response over a concentration range covering at least three orders of magnitude. Furthermore, the lowest concentration injected was far from the minimum detectable concentration and so the linear dynamic range is likely to be closer to four orders of magnitude, possibly even five.

Figure 10:
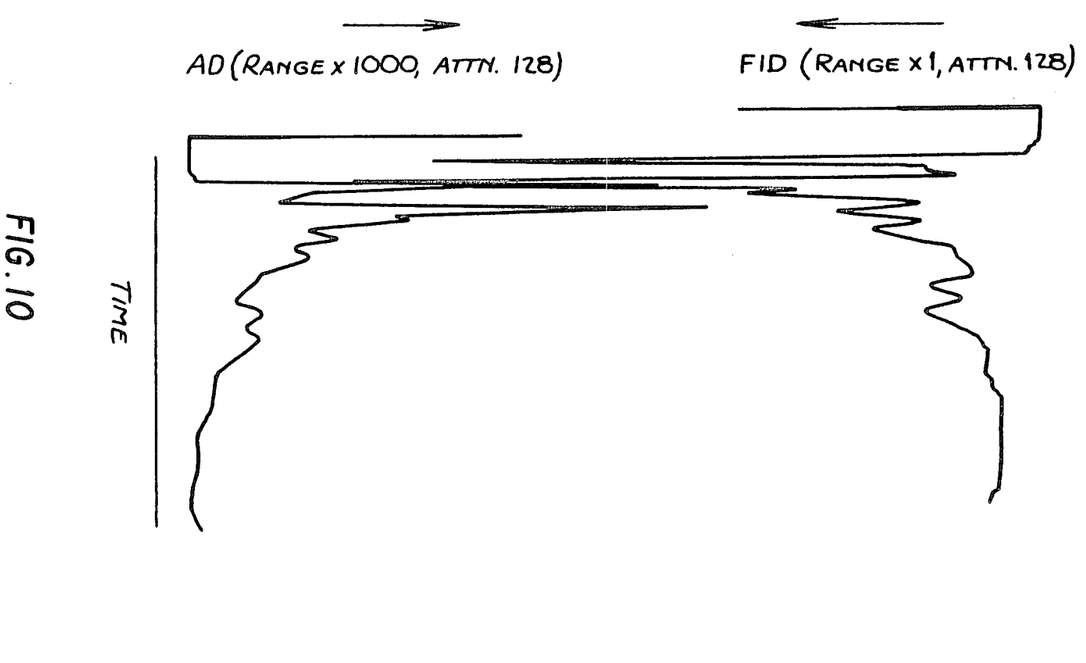
FIG. 10 are respective chromatograms of a hydrocarbon mixture obtained by means of a detector embodying the present invention and with a flame ionization detector.
Figure 11:
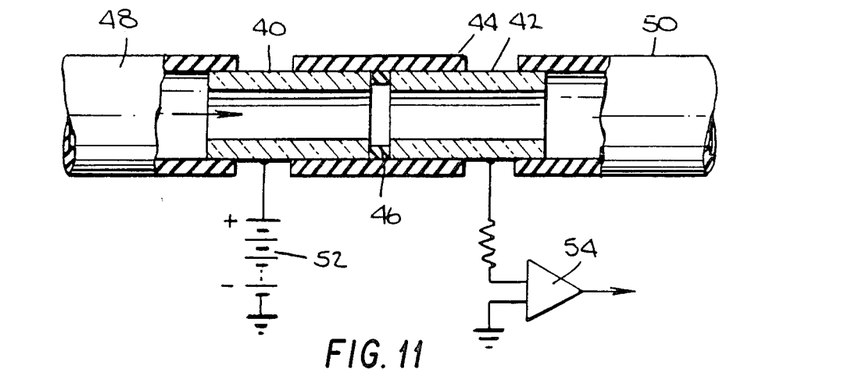
FIG. 11 is a cross-section of a modified version of a noble gas detector in accordance with the invention.

FIG. 11 illustrates a modified version of a noble gas detector in accordance with the present invention. It comprises a pair of glass tubes 40, 42 which are held in alignment by a PTFE sleeve 44, their ends being separated by a washer 46 of PTFE or other non-conductive material such as quartz or fused silica. The ID of washer 46 is larger than that of the walls of the glass tubes so that areas of the separated glass ends face each other. The gap between the ends created by washer 46 is preferably 0.5–1.0 mm. An inlet tube 48 and an outlet tube 50 permit the passage of effluent from a chromatographic column therethrough as shown by the arrow. The two glass tubes 40, 42 are connected in series with a power supply 52 and an amplifier 54 supplying a recorder (not shown). The power supply may be 1,000–2,000 volts. The detector of FIG. 10 has been found to be operable with both argon and helium at temperatures at least as low as 120° C.

FIG. 12 is a reproduction of a chromatogram obtained from a helium detector operating at a temperature of 180° C. and a voltage of 1,700 volts. It is compared with the output of a flame ionization detector as previously described relative to FIG. 5.

From the foregoing description, a noble gas detector, employing the evolution of electrons in a glass envelope at elevated temperatures, has been shown to function satisfactorily as a gas chromatograph detector. Detector sensitivity appears to be an order of magnitude greater than that of a flame ionization detector with a linear dynamic range approaching four orders of magnitude. It will be obvious that a number of detector geometries may be employed. In this way, a detector of very small volume may be constructed suitable for direct in-line use with capillary columns. Furthermore, the detector may be constructed entirely of non-metallic materials such as glass and PTFE and is, accordingly, a very inert device. This could be of significant advantage.

The evolution of electrons within a glass envelope at elevated temperatures has been confirmed, and this effect has been used to build and operate a noble gas detector with both argon and helium. The detector provided a linear response over at least three orders of magnitude and exhibited a sensitivity of at least one order of magnitude greater than that of a flame ionization detector. It exhibited sensitivity and linearity adequate for general use in gas chromatography and, at the same time, utilized a simplified pneumatic gas supply. This provides a basis for additional reduction in instrument cost.

It will be apparent that a number of variations and modifications may be made in this invention without departing from its spirit and scope. Accordingly, the foregoing description is to be construed as illustrative only, rather than limiting. This invention is limited only by the scope of the following claims.

What is claimed is:

1. For use in gas chromatography, a detector of the type including a detection chamber, means for establishing an electrical potential across said chamber, and means for causing evolution of free electrons in said chamber, the improvement wherein the electron evolution causing means comprises:

a noble gas within said chamber;

a volume of glass having a surface in said chamber in contact with said noble gas, at least said surface of the glass having been subjected to preconditioning treatment for stabilizing its emissivity of electrons; and means for heating said glass and noble gas to a temperature sufficient to induce evolution of electrons therefrom.

2. The improvement defined in claim 1 wherein said preconditioning treatment comprises contacting at least said surface with an alkali metal salt.

3. The improvement defined in claim 2 wherein said alkali metal salt is lithium nitrate.

4. The improvement defined in claim 1 wherein said treatment comprises aging said glass for a period of time sufficient to effect said stabilization of electron emissivity.

5. The improvement defined in claim 4 wherein said aging is at a temperature of at least about 250° C.

6. The improvement defined in claim 1 wherein said heating means is adapted to maintain said temperature between 100° C. and 300° C.

7. The improvement defined in any one of the preceding claims wherein the glass is selected from the group consisting of soda glass and borosilicate glass.

8. The improvement defined in any one of the preceding claims 1–6 wherein said noble gas is selected from the group consisting of argon and helium.

9. A method for analyzing the effluent from a gas chromatographic column while employing a noble gas carrier to elute sample gases therefrom which comprises:

passing said effluent through an ionization region in the presence of glass;

heating said glass and noble gas to evolve free electrons within the ionization region for raising the noble gas atoms to their metastable states;

preconditioning at least the surface of said glass contacted by said noble gas to stabilize its emissivity;

allowing the metastable noble gas atoms to collide with molecules of sample gas to ionize the sample gas molecules; and measuring the concentration of ionized sample gas molecules in said ionization region.

10. The improvement defined in claim 9 wherein said preconditioning treatment consists of aging said glass at a temperature of at least about 250° C.

11. The improvement defined in claim 10 wherein said preconditioning treatment consists of contacting said glass with an alkali metal salt.

12. The improvement defined in claim 11 wherein said salt is fused lithium nitrate.

13. The improvement defined in any one of the preceding claims wherein said noble gas is selected from the group consisting of argon and helium.

14. The improvement defined in any one of the preceding claims 9–12 wherein said glass is selected from the group consisting of soda glass and borosilicate glass.

* * * * *